United States Patent
Yunlu et al.

(10) Patent No.: US 7,312,251 B2
(45) Date of Patent: Dec. 25, 2007

(54) SYNTHESIS OF STABLE SOLUTIONS OF RARE EARTH TRIS (ORGANOPHOSPHATE) IN HYDROCARBON SOLVENTS

(75) Inventors: Kenan Yunlu, Princeton, NJ (US); Min He, East Windsor, NJ (US)

(73) Assignee: Rhodia Rare Earths, Inc., Shelton, CT (US)

( * ) Notice: Subject to any disclaimer, the term of this patent is extended or adjusted under 35 U.S.C. 154(b) by 666 days.

(21) Appl. No.: 10/819,608

(22) Filed: Apr. 7, 2004

(65) Prior Publication Data

US 2004/0192950 A1    Sep. 30, 2004

Related U.S. Application Data

(62) Division of application No. 09/557,719, filed on Apr. 25, 2000, now Pat. No. 6,767,927.

(60) Provisional application No. 60/131,331, filed on Apr. 26, 1999.

(51) Int. Cl.
*B01F 3/12* (2006.01)
*C07F 9/02* (2006.01)
*C09K 3/00* (2006.01)

(52) U.S. Cl. ............................ 516/33; 516/31; 534/15; 556/2; 556/5; 556/15; 556/19; 556/24; 558/71; 558/89; 568/8; 252/189

(58) Field of Classification Search ................ 556/24
See application file for complete search history.

(56) References Cited

U.S. PATENT DOCUMENTS

| | | | | |
|---|---|---|---|---|
| 3,047,601 A | * | 7/1962 | Johnson | 423/10 |
| 3,110,556 A | * | 11/1963 | Peppard et al. | 423/21.5 |
| 3,539,941 A | * | 11/1970 | Halverson | 372/52 |
| 3,551,345 A | * | 12/1970 | Kleinerman | 252/301.18 |
| 4,242,232 A | | 12/1980 | Sylvester et al. | |
| 4,429,089 A | | 1/1984 | Pedretti et al. | |
| 4,619,982 A | | 10/1986 | Jenkins | |
| 4,749,560 A | * | 6/1988 | Elgavish | 424/9.36 |
| 4,791,086 A | | 12/1988 | Yeh et al. | |
| 5,057,627 A | * | 10/1991 | Edwards | 568/618 |
| 5,064,910 A | | 11/1991 | Hattori et al. | |
| 5,130,052 A | * | 7/1992 | Kreh et al. | 252/387 |
| 5,306,746 A | * | 4/1994 | Ida et al. | 523/206 |
| 5,478,901 A | | 12/1995 | Jones et al. | |
| 5,674,985 A | * | 10/1997 | Hawkins et al. | 534/16 |
| 5,858,465 A | * | 1/1999 | Hunt et al. | 427/248.1 |

FOREIGN PATENT DOCUMENTS

| | | |
|---|---|---|
| EP | 0 520 732 A1 | 12/1992 |
| EP | 0 924 214 A3 | 6/1999 |

OTHER PUBLICATIONS

Suglobov D.N. et al.: "DEHP Complexes of Lanthanides (III) and Actinides (III)" Journal of Alloys and Compounds, CH, Elsevier Sequoia, Lausanne, vol. 213/214, 1994, pp. 523-527, XP000907646, ISSN: 0925-8388.

* cited by examiner

*Primary Examiner*—Joseph D. Anthony
(74) *Attorney, Agent, or Firm*—Daniel P. Cillo; Eckert Seamans Cherin & Mellott, LLC

(57) ABSTRACT

Stable rare earth tris (organophosphate) solutions comprise a rare earth tris (organophosphate) and a hydrocarbon solvent. From about 2% to about 10% rare earth element, preferably from about 3% to about 8%, is present in the solutions. The rare earth tris (organophosphate) solutions are stable from precipitation of the rare earth tris (organophosphate) for at least about fifteen (15) days, preferably for at least about twenty (20) days and most preferably at least about thirty (30) days. A process for preparing these solutions is described herein. A stabilizing additive, acid, glycol or mixtures thereof, is utilized to inhibit precipitation. The molar ratios of free acid, glycol and/or water to the rare earth element are controlled to inhibit precipitation.

2 Claims, No Drawings

SYNTHESIS OF STABLE SOLUTIONS OF RARE EARTH TRIS (ORGANOPHOSPHATE) IN HYDROCARBON SOLVENTS

CROSS REFERENCE TO RELATED APPLICATION

This application is a divisional application of U.S. Pat. No. 6,767,927 B2. U.S. Ser. No. 09/557,719 filed on Apr. 25, 2000, and also claims the benefit of U.S. Provisional Application Ser. No. 60/131,331 filed Apr. 26, 1999.

FIELD OF THE INVENTION

The invention relates to the production of stable solutions of rare earth tris (organophosphates) in a hydrocarbon solvent.

BACKGROUND INFORMATION

The production of rare earth tris (organophosphates), particularly rare earth alkylphosphates, in various solvents is generally a straightforward process. Due to their low solubility in water and common organic solvents, the rare earth tris (organophosphates) precipitate easily. The poor solubility of these compositions is noted in the article, "DEHP complexes of lanthanides (III) and actinides (III)," Suglobov et al., Journal of Alloys and Compounds, 213/214 (1994) 523-527. Suglobov et al. point out that "$LnA_3$ (A=dialkylphosphate) is very poorly soluble in alkanes as well as in donor solvents." See the Abstract page 523 of Suglobov et al. The lower solubility of the rare earth tris (organophosphates) in hydrocarbon solvents, compared to, for instance, rare earth neo acid complexes, is mainly due to the presence of the phosphorous atoms which considerably lowers the organic character of the molecule. Providing rare earth tris (organophosphates) in a hydrocarbon solvent is desirable for manufacturers utilizing the rare earth tris (organophosphates) for preparation of catalysts. If the rare earth tris (organophosphates) could be stable in the hydrocarbon solvent, i.e., not precipitate over an extended period of time, such a product would be very beneficial for the manufacturing formulator.

It is an aspect of the present invention to produce solutions comprising a rare earth tris (organophosphate) and a hydrocarbon solvent wherein said solutions are stable from precipitation of the rare earth tris (organophosphate) for at least about thirty days.

It is another aspect of the present invention to introduce a process, which by a combination of beneficial experimental conditions, allows the production of highly stable solutions of a rare earth tris (organophosphate) in a hydrocarbon solvent.

These and other aspects of the invention are discussed in detail below.

SUMMARY OF THE INVENTION

The stable rare earth tris (organophosphate) solutions comprise a rare earth tris (organophosphate) and a hydrocarbon solvent. Preferably, from about 2% to about 10% rare earth element, preferably from about 3% to about 8%, is present in the solutions. Unless otherwise stated, all parts, ratios or percents are by weight. The rare earth tris (organophosphate) solutions are stable from precipitation of the rare earth tris (organophosphate) for at least about fifteen (15) days, preferably for at least about twenty (20) days and most preferably at least about thirty (30) days. A process for preparing these solutions is described herein.

As used herein, "alkyl" means a carbon-containing chain which may be straight, branched or cyclic; substituted (mono- or poly-) or unsaturated; and saturated.

As used herein, "aryl" means an aromatic; substituted (mono- or poly-) or unsaturated.

As used herein, "free acid" means the $H^+$ concentration as measured by conventional methods.

As used herein, the terms "rare earth tris (organophosphate)", "organophosphate", "alkylphosphate", "base", "stabilizing additive" and "rare earth salt" shall encompass the singular and plural, as well as, to encompass mixtures of the respective compounds.

"Comprising" as used herein, means various components can be conjointly employed. Accordingly, the terms "consisting essentially of" and "consisting of" are embodied in the term comprising.

DETAILED DESCRIPTION OF THE INVENTION

In preparing the rare earth tris (organophosphate) solutions, an organophosphate salt solution is preferably prepared by reaction of the organophosphate with a base, which is an ammonium (preferably tetra (lower alkyl) ammonium) oxide or hydroxide, sodium oxide or hydroxide, or mixtures thereof. Sodium bases are generally not recommended for use due to their contribution to the formation of solutions having a high viscosity, e.g., greater than about 1000 cps. Most preferably, the base is ammonium hydroxide. Bases suitable for use include: sodium hydroxide, ammonium hydroxide, tetrabutyl ammonium hydroxide, tetra methyl ammonium hydroxide, tetra ethyl ammonium hydroxide. The reaction of the organophosphate and base is generally in the presence of a solvent selected from the group consisting of: water, hydrocarbon solvent or mixtures thereof. Preferably, the reaction occurs in the presence of a hydrocarbon solvent. A suitable hydrocarbon solvent can be selected from the group consisting of hexanes, cyclohexane, heptane, methyl pentane, methyl cyclopentane, n-hexane, pentane, toluene, 3-methylpentane, 2-methylpentane, 2,3-dimethylpentane and isomers and mixtures thereof. A preferred hydrocarbon solvent is selected from the group consisting of hexanes, cyclohexane, heptane and isomers and mixtures thereof. Commercially available hydrocarbon solvents are EXXSOL® hexanes supplied by Exxon, EXXSOL® heptane supplied by Exxon, ISOPAR-G® hydrocarbon solvent supplied by Exxon, ISOPAR-M® hydrocarbon solvent supplied by Exxon, ISOPAR-L® hydrocarbon solvent supplied by Exxon, SOLVENT 140® hydrocarbon solvent supplied by Exxon, and MINERAL SPIRITS 66® hydrocarbon solvents supplied by Philips.

The pH of the organophosphate salt solution preferably ranges from about 5.0 to about 9.0, more preferably from about 5.5 to about 7.0 and most preferably from about 6.0 to about 6.5.

The temperature of the reaction of the organophosphate with the base is believed to not be critical and reaction temperatures can vary. Generally, the reaction can be carried out at room temperature, e.g., about 25° C.

The organophosphate salt solution is then reacted with a rare earth salt to produce the crude rare earth tris (organophosphate) solution. For this purpose the organophosphate salt solution is charged with an aqueous solution of the desired rare earth salt or salts ("rare earth salt solution").

It has been discovered that it is beneficial for the stability of the product to utilize a low addition rate. The addition rate for the rare earth salt solution (which preferably having a rare earth content of from about 23% to about 26%) is a rate sufficient to achieve the desired viscosity of the desired rare earth tris (organophosphate) solution. For compostions having a viscosity of less than about 600 cps, the rate can range from about 1 to 2 hours.

The temperature of the reaction of the organophosphate salt solution with the rare earth salt solution is preferably greater than about 30° C., more preferably greater than about 40° C. and most preferably from about 40° C. to about 60° C.

The rare earth salts suitable for use are the salts of group III B of the periodic table (lanthanide series). Rare earth elements are a group of fifteen chemically related elements in Group IIIB of the periodic table (lanthanide series). The suitable lanthanide series rare earth elements comprise: lanthanum, cerium, praseodymium, neodymium, samarium, europium, gadolinium, terbium, dysprosium, holmium, erbium, thulium, ytterbium, lutetium, yttrium, scandium and mixtures thereof. Preferred rare earth elements for use are neodymium, lanthanum, praseodymium, cerium (preferably Ce III) and mixtures thereof. Most preferred is lanthanum. Due to the nature of the ores from which these rare earth raw materials are made, minor amounts of other rare earth elements can be present in a desired rare earth salt or rare earth salt solution. Preferred grades for use herein are greater than about 90% by weight of the desired rare earth element or salt, e.g., rare earth nitrate, rare earth chloride, rare earth oxide, rare earth hydroxide, rare earth acetate, rare earth oxychloride, rare earth oxynitrate, and mixtures thereof.

For example, suitable rare earth salts comprise: rare earth nitrates, rare earth chlorides, rare earth acetates, rare earth hydroxides, rare earth oxides, rare earth oxychlorides, rare earth oxynitrates, and mixtures thereof. Preferred rare earth salts are rare earth nitrate, rare earth chloride, and mixtures thereof. Most preferred for use are rare earth nitrates, for example, the nitrates of lanthanum, cerium, praseodymium, neodymium, samarium, europium, gadolinium, terbium, dysprosium, holmium, erbium, thulium, ytterbium, lutetium, yttrium, scandium and mixtures thereof. Preferably, an aqueous solution of the rare earth salt can be utilized.

Organophosphate compounds comprise: diesters of phosphoric acid, (RO)(R'O)PO(OH) [R=alkyl, aryl, and combinations thereof; R'=alkyl, aryl and combinations thereof]; the monoesters of phosphoric acid (RO) PO(OH)$_2$ [R alkyl, aryl and combinations thereof]; phosphonates of the general formula (RO)R'P(O) and RP(O)(OH)$_2$ [R=alkyl, arlyl and combinations thereof]; phosphinates of the general formula R(R')P(O)OH and R(H)P(O)OH [R=alkyl, aryl and combinations thereof]; and mixtures thereof.

Preferred organophosphate compounds are the diesters of phosphoric acid, (RO)(R'O)PO(OH) [R=n-butyl, isobutyl, pentyl, amyl, isopentyl, 2,2-dimethylhexyl, 2-ethylhexyl, 1-ethylhexyl, tolyl, nonaphenoxyl and combinations thereof; R'=n-butyl, isobutyl, pentyl, amyl, isopentyl, 2,2-dimethylhexyl, 2-ethylhexyl, 1-ethylhexyl, tolyl, nonaphenoxyl and combinations thereof]; the monoesters of phosphoric acid (RO) PO(OH)$_2$ [R=n-butyl, isobutyl, pentyl, amyl, isopentyl, 2,2-dimethylhexyl, 2-ethylhexyl, 1-ethylhexyl, tolyl, nonaphenoxyl]; phosphonates of the general formula (RO) R'P(O) and RP(O)(OH)$_2$ [R=n-butyl, isobutyl, pentyl, amyl, isopentyl, 2,2-dimethylhexyl, 2-ethylhexyl, 1-ethylhexyl, tolyl, nonaphenoxyl and combinations thereof]; phosphinates of the general formula R(R')P(O)OH and R(H)P(O)OH [R=n-butyl, isobutyl, pentyl, amyl, isopentyl, 2,2-dimethylhexyl, 2-ethylhexyl, 1-ethylhexyl, tolyl, nonaphenoxyl and combinations thereof]; and mixtures thereof.

The organophosphate salt solution and the rare earth salt solution are reacted. An aqueous phase and an organic phase will be present in the reaction product. The aqueous phase is removed. A conventional method for removal of the aqueous phase can be utilized, such as a liquid—liquid extraction. Preferably, the organic phase is then washed with water. The crude liquid can then be adjusted for water and free acid content by conventional means to achieve the appropriate molar ratio of water to rare earth element and/or free acid to rare earth element. For example, the concentration of water can be adjusted by azeotropic distillation and/or by the addition of water. The free acid concentration can be adjusted by addition of a carboxylic acid and/or another stabilizing acid.

A stabilizing additive is added. The stabilizing additive can be: water, phosphoric acids and esters thereof, sulfuric acids and esters thereof, boric acids and esters thereof, glycols (diols) and their ether derivatives, and mixtures thereof. The stabilizing additive is preferably added after the removal of the aqueous phase, after any washing of the organic phase, and before any adjustment of the water content by azeotropic distillation, for example.

The viscosity of the final rare earth tris (organophosphate) solution is preferably less than about 600 cps, more preferably less than about 500 cps and most preferably less than about 100 cps.

The preferred process for production of a stable rare earth tris (organophosphate) solution is illustrated by the following description for the preparation of a lanthanum tris (di-2-ethylhexylphosphate) of the present invention.

The reaction can be represented as follows:

1. Salt formation in hydrocarbon/water mixture

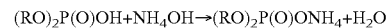

di-2-ethylhexylphosphate ammoniumdi-2-ethylhexylphosphate

2. Formation of the rare earth di-2-ethylphosphate in water/hydrocarbon solvent

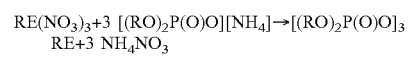

RE nitrate RE di-2-ethylhexylphosphate
RE=La; R=2-ethylhexyl-

The rare earth tris (organophosphate) is prepared in a two solvent system by mixing the rare earth nitrate solution and the organophosphate salt solution. The resulting aqueous phase (layer) is discarded. The organic phase may be washed with water. The remaining organic solution comprises in addition to the rare earth tris (organophosphate) complex, certain quantities of water and free acid.

It has been discovered that acids present and measurable in the solution as free acid, glycols and or other stabilizing additives are highly effective in stabilizing the solutions of rare earth, preferably La, tris (organophosphate), in hydrocarbon solvents. These stabilizing additives aid in inhibiting the precipitation of the rare earth tris (organophosphate) from the solution.

Solutions which do not contain any stabilizing additive, any glycol and or free acid for example, form precipitates rapidly. Compositions of the present invention are generally stable for at least about three (3) days, preferably at least about seven (7) days, and most preferably at least about fourteen (14) days. Preferred compositions are stable for at least about fifteen (15) days, preferably for at least about twenty (20) days and most preferably at least about thirty (30) days.

It is essential for stability that the rare earth tris (organophosphate) solutions have an appropriate glycol to rare earth element molar ratio and/or free acid to rare earth element molar ratio. Preferably, both the glycol to rare earth element molar ratio and the free acid to rare earth element molar ratio are within the ranges specified herein.

One skilled in the art will recognize that conventional methods can be utilized to adjust the molar ratios for glycol, free acid or glycol and free acid after the production of the rare earth tris (organophosphate). Preferably, the ratios are adjusted by the addition of a stabilizing additive selected from the group comprising: acid, glycol and mixtures thereof.

Acid can provide stabilizing benefits to the rare earth tris (organophosphate) solutions. Acids suitable for use are organic acids which are compatible with the combined organic solvent and rare earth tris (organophosphate). Compatibility means the organic acid is soluble to a degree necessary to achieve the requisite free acid concentration. One skilled in the art is capable of making this determination. Particularly, the molar ratio of free acid to rare earth element within certain ranges can provide improved stability for the highly concentrated rare earth tris (organophosphate) solutions, e.g., greater than about 8% rare earth element. To achieve the desired free acid ratio, an acid is used. Acids suitable for use include: acids and esters based on phosphorus compounds, acids and esters based on sulfur compounds, acids and esters based on boron compounds, and mixtures thereof. The rare earth tris (organophosphate) solutions of the present invention can have a molar ratio of free acid to rare earth element of less than or equal to about 5, preferably less than or equal to about 2 and most preferably less than or equal to about 1.

Acids and esters based on phosphorus compounds suitable for use include: phosphoric acid ($H_3PO_4$); mono and di alkyl esters of phosphoric acid (e.g., $R^1H_2PO_4$ and $R^1R^2HPO_4$ wherein $R^1$ and $R^2$ are methyl, ethyl, propyl, iso-propyl, butyl, pentyl, hexyl, 2-ethylhexyl and combinations thereof); o-phosphorous acid ($H_3PO_3$); metaphosphoric acid; mono alkyl phosphonic acids (e.g., $RH_2PO_3$ wherein R is methyl, ethyl, or 1-propyl); mono esters of alkyl phosphonic acid (e.g., $R\,R^1\,HPO_3$ wherein R is methyl, ethyl, and 1-propyl and $R^1$ is methyl, ethyl, propyl, iso-propyl, butyl, pentyl, hexyl, 2-ethylhexyl, and combinations thereof); organic derivatives of phosphinic acid (e.g., $R\,R^1\,HPO_2$ wherein R and $R^1$ are methyl, ethyl, propyl, iso-propyl, butyl, pentyl, hexyl, 2-ethylhexyl and combinations thereof); and mixtures thereof.

Acids and esters based on sulfur compounds suitable for use include: sulfuric acid; pyrosulfuric acid; alkane and arene sulfonic acids (e.g., $RSO_3H$ wherein R is methane, ethane, n-propane, z-propane, butane, pentane, hexane, trifluoromethane, benzene, 3,5-dimethylbenzone, m-nitrobenzene, 2-aminobenzene, 3-aminobenzene, p-dodecylbenzene, p-toluene, 1-naphthalene, 2-naphthalene, 2-acrylamidopropane, 2-acrylamido-2-methylpropane, 2-methacrylamids-2-methylpropane, 3-acrylamido-2,4,4-trimethylpentane, 2-acrylamido-2-phenylethane, 2-acrylamido-2-phenylpropane, 2-acrylamido-2-(p-tolyl)ethane, sulfamic acid ($H_2NSO_3H$); sulfanilic acid ($4-(H_2N)C_6H_4SO_3H$); alkane and arene sulfinic acids (e.g., $RSO_2H$ wherein R is methane or benzene); and mixtures thereof.

Acids based on boron compounds suitable for use include: boric acid ($B(OH)_3$) and metaboric acid ($HBO_2$).

The acid can be used before, during or after the preparation of the rare earth tris (organophosphate). Preferably, acid is utilized during or after the preparation. Most preferably, the acid is added after the formation of the rare earth tris (organophosphate). The acid can be added in a single stage or in several stages. For example, an acid can be utilized to produce the organophosphate salt solution, and if required, additional acid can be added after preparation to achieve a suitable molar ratio. An excess of acid can be utilized in the formation of the organophosphate salt solution to provide a stabilizing free acid molar ratio. Acids can be used in combination or separately. When utilizing combinations, the acids can be premixed and added simultaneously, or added separately. The acid can be added in the form of the acid or as a salt of the acid.

Glycols (diols) and their ether derivatives can also stabilize rare earth tris (organophosphate) solutions provided they are compatible with the combined organic solvent and rare earth tris (organophosphate). Compatibility means the glycol is soluble to a degree necessary to achieve the requisite glycol concentration. One skilled in the art is capable of making this determination. Particularly, the molar ratio of glycol to rare earth element within certain ranges can provide improved stability for the rare earth tris (organophosphate) solutions. The glycol concentration can be determined by conventional chromatography methods (e.g. GC). Glycols and their ether derivatives suitable for use include: propylene glycol (1,2-propanediol), di(propylene glycol), ethylene glycol (1,2-ethanediol), di(ethylene glycol), 1,2- and 1,3- and 1,4-butanediol, ethylene glycol dimethyl ether, ethylene glycol diethyl ether, ethylene glycol dipropyl ether, ethylene glycol dibutyl ether, ethylene glycol ethyl ether, ethylene glycol butyl ether, ethylene glycol tert-butyl ethyl ether, ethylene glycol tert-butyl methyl ether, ethylene glycol butyl vinylether, ethylene glycol diglycidyl ether, propylene glycol dimethyl ether (1,2-dimethoxypropane), 2,2-diethoxypropane, 3,3-diethoxy-1-propanol, propylene glycol butyl ether, propylene glycol monomethyl ether (1-methoxy-2-propanol), propylene glycol phenyl ether, propylene glycol propyl ether, and mixtures thereof. Preferred, glycols are selected from the group consisting of: di(propylene glycol), propylene glycol, ethylene glycol, di(ethylene glycol) and mixtures thereof.

Preferably, the glycol can be used during or after the preparation of the rare earth tris (organophosphate). The glycol can be added in a single stage or in several stages. In addition, the glycol can be used in combination or separately. When utilizing combinations, the glycol can be premixed and added simultaneously, or added separately. Preferably, the glycol is added after formation of the rare earth tris (organophosphate). The rare earth tris (organophosphate) solutions of the present invention can have a ratio of stabilizing additive, glycol (diols) and their ether derivatives, to rare earth element of less than or equal to about 5, preferably less than or equal to about 2 and most preferably less than or equal to-about 1.

It has been also discovered that water provides to a lesser degree stabilizing benefits to rare earth tris (organophosphate) solutions than it does, for instance, to rare earth carboxylate solutions. In fact, water can cause an increase in the viscosity of rare earth tris (organophosphate) solutions. To achieve the appropriate molar ratio of water to rare earth element, water can be removed using conventional means such as azeotropic distillation. The molar ratio of water to rare earth element is preferably less than or equal to about 2, more preferably less than or equal to about 0.1 and most preferably less than or equal to about 0.05.

A preferred embodiment, rare earth alkylphosphonates are prepared with di-2-ethylhexylphosphoric acid. The general formula of lanthanum tris (di-2-ethylhexylphosphate) is $LaC_{48}H_{102}P_3O_{12}$.

The basic, general structure of this complex is:

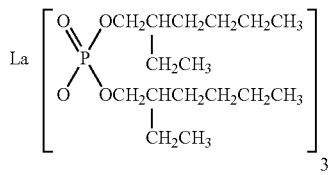

The La tris (di-2-ethylhexylphosphate) solutions of the present invention comprise from about 2% to about 10%, preferably from about 3% to about 8% and most preferably from about 3.5% to about 5% La by weight. Preferably, the La tris (di-2-ethylhexylphosphate) solutions are prepared utilizing hexanes, cyclohexane, methylpentane, as well as, isomers and mixtures thereof, as the solvent.

The La tris (di-2-ethylhexylphosphate) solutions have a molar ratio of free acid to rare earth element, La, of less than or equal to about 5, preferably less than or equal to about 2 and most preferably less than or equal to about 1. The molar ratio of water to rare earth element, La, is less than or equal to about 2, preferably less than or equal to about 0.1 and most preferably less than or equal to about 0.05. The molar ratio of glycol(diols) and their ether derivatives to rare earth element, La, is less than or equal to about 5, preferably less than or equal to about 2 and most preferably less than or equal to about 1.

Further, the rare earth tris (organophosphate) solutions can provide excellent properties as raw materials for making catalysts for diene polymerization.

The following example is provided to better describe and define the process and product of the present invention. It is for illustrative purposes and that various modifications or changes in light thereof may be suggested to one skilled in the art and are still considered to fall within the spirit and purview of this application and scope of the appended claims.

EXAMPLE

The following example illustrates a procedure for preparing a solution of lanthanum tris (di-2-ethylhexylphosphate) of the present invention:

In a 2-liter reactor, an ammonium di-2-ethylhexylphosphate/hexane/water solution having a pH range of from about 5.5 to about 6.5 (at about 50° C.) is prepared by adding of about 56 g of ammonia solution (about 29.6%) dropwise to a clear solution of about 312 g di-2-ethylhexylphosphoric acid (MW321.8) in about 650 g of hexanes at temperatures of from about 45 to about 50° C. The clear, colorless solution is then charged with an aqueous La nitrate solution (about 191 g; La content about 23.53%). The latter is added dropwise under vigorous mixing, while keeping the rate of addition about 1 ml/min and the temperature at about 50° C. The product dissolves quickly in the organic layer. After complete addition, the mixture is stirred for an additional 60 minutes and the aqueous layer is discarded. The organic layer is washed with 3×250 mil water. The crude lanthanum tris (di-2-ethylhexylphosphate) solution is analyzed to contain about 1.1% water. At this point dipropylene glycol is added to achieve the desired quantity of about 1.5%. The reactor is then equipped with a Dean-Stark adapter and the required quantity of water removed by azeotropic distillation. The final product is a stable, clear, colorless solution. The yield is about 950 g. Analysis determines the product to have:

| | |
|---|---|
| La | about 4.2% |
| P | about 3.2% |
| free acid | about 4.3% |
| water | about 94 ppm |
| viscosity | about 86 cPs (25° C., Brookfield) |
| Free di-2-ethylhexylphosphoric acid/La molar ratio: | about 4.3 g/321.97 = 0.013 m (321.97 = mol. weight of di-2-ethylhexylphosphoric acid) |
| | about 4.2 g/138.91 = 0.03 m (138.91 = atomic weight of La) |
| | about 0.013/0.03 = 0.43 |
| Water/La molar ratio: | about 0.094 g/18 = 0.005 (18 = mol. weight of water) |
| | about 4.2 g/138.91 = 0.03 m (138.91 = atomic weight of La) |
| | about 0.005/0.03 = 0.17 |

Whereas particular embodiments of this invention have been described above for purposes of illustration, it will be evident to those skilled in the art that numerous variations of the details of the present invention may be made without departing from the invention as defined in the appended claims.

What is claimed is:

1. A product solution comprising:
   (a) a component selected from the group consisting of: rare earth tris (organophosphate), rare earth tris (organophosphonate) and rare earth tris (organsphosphinate) and mixtures thereof;
   (b) a hydrocarbon solvent;
   (c) water; and
   (d) a stabilizing additive selected from the group consisting of:
   propylene glycol (1,2-propanediol), di(propylene glycol), ethylene glycol (1,2-ethanediol), di(ethylene glycol), 1,2- and 1,3- and 1,4-butanediol, ethylene glycol dimethyl ether, ethylene glycol diethyl ether, ethylene glycol dipropyl ether, ethylene glycol dibutyl ether, ethylene glycol ethyl ether, ethylene glycol butyl ether, ethylene glycol tert-butyl ethyl ether, ethylene glycol tert-butyl methyl ether, ethylene glycol butyl vinylether, ethylene glycol diglycidyl ether, propylene glycol dimethyl ether (1,2-dimethoxypropane), 2,2-diethoxypropane, 3,3-diethoxy-1-propanol, propylene glycol butyl ether, propylene glycol monomethyl ether (1-methoxy-2-propanol), propylene glycol phenyl ether, propylene glycol propyl ether, phosphoric acid ($H_3PO_4$), moho and di alkyl esters of phosphoric acid, o-phosphorous acid ($H_3PO_3$), metaphosphoric acid, mono alkyl phosphonic acids, mono esters of alkyl phosphonic acid, organic derivatives of phosphinic acid, sulfuric acid, pyrosulfuric acid, alkane and arene sulfonic acids, sulfanilic acid (4-($H_2N$)$C_6H_4SO_3H$), alkane and arene sulfinic acids, boric acid ($B(OH)_3$), metaboric acid ($HBO_2$), and mixtures thereof;
   wherein the molar ratio of water to rare earth element is less than or equal to about 2 and the molar ratio of stabilizing additive to rare earth element is less than or equal to about 5, and wherein component (a) is free from precipitation from the solution for at least about twenty (20) days.

2. A product solution according to claim 1 wherein component (a) is free from precipitation from the solution for at least about thirty (30) days.

* * * * *